United States Patent [19]

Berman et al.

[11] Patent Number: 4,503,142
[45] Date of Patent: Mar. 5, 1985

[54] OPEN READING FRAME VECTORS

[75] Inventors: Michael L. Berman, Damascus; Thomas J. Silhavy, Middletown; George M. Weinstock, Frederick, all of Md.

[73] Assignee: Litton Bionetics, Inc., Kensington, Md.

[21] Appl. No.: 392,308

[22] Filed: Jun. 25, 1982

[51] Int. Cl.³ .................. C12P 21/00; C12P 21/02; C12P 19/34; C12Q 1/68; C12Q 1/00; C12Q 1/34; C12N 15/00; C12N 1/20; C12N 1/00; C07H 21/04

[52] U.S. Cl. .................. 435/6; 435/68; 435/70; 435/91; 435/172.3; 435/253; 435/317; 435/4; 435/18; 536/27; 436/536; 436/804

[58] Field of Search .................. 435/317, 253, 68, 70, 435/91, 6, 172, 172.3, 4, 7, 18; 536/27; 436/536, 804

[56] References Cited

U.S. PATENT DOCUMENTS 4,356,270 10/1982 Itakura .................. 435/172
4,366,246 12/1982 Riggs .................. 435/172

OTHER PUBLICATIONS

Hall et al., J. Mol. Biol. 146, 23, (1981).
Mutoh et al., FEBS Lett. 137, 171, (1982).
Villa-Komoroff et al., Proc. Natl. Acad. Sci. USA 75, 3727, (1978).
Broome et al., Proc. Natl. Acad. Sci. USA 75, 2746, (1978).
Bedovelle, Nature, 285, 78, (1980).
Bolivar, Gene, 2, 95, (1977).
Casadaban, J. Bact., 143, 971, (1980).
Ruther, Molec. Gen. Genet., 178, 475, (1980).
Wagner, Proc. Nat. Acad. Sci. USA, 78, 1441, (1981).

Primary Examiner—Thomas G. Wiseman
Assistant Examiner—James Martinell
Attorney, Agent, or Firm—Spencer & Frank

[57] ABSTRACT

An open reading frame DNA vector is presented having a promoter-translation start region, and adjacent thereto and downstream therefrom, a first coding segment having a start codon, a second coding segment coding for detectable protein, and an insertion region between said first and second coding regions having an insertion site and being of such length that the first and second coding segments are not in reading frame phase with each other. A method for the cloning and positive selection of a DNA segment having an open reading frame is also presented, as well as a tribrid protein wherein each terminal region and the mid-section is derived from a different gene, and a method of identifying and quantifying a protein or polypeptide without regard to its structure or biological function by using a DNA segment coding for said protein or polypeptide as the mid-section of the tribrid protein.

15 Claims, 4 Drawing Figures key to sites:  P = PstI, A = AccI, S = SalI, H = HincII
               Sm = SmaI, X = XmaI, E = EcoRI Sequence of sites around Kan$^r$:

```
                HincII                                    HincII
                Acc I                                     Acc I
EcoRi    BamHI  Sal I Pst I                       Pst I Sal I  BamHI       Eco RI
GAATTCCCGGGCATCCGTCGACCTGCAGGGG---  Kan$^r$  ---CCCCTGCAGGTCGACGGATCCCCGGGAATTC
    Sma I                                                          Sma I
    Xma I                                                          Xma I
```

OPEN READING FRAME VECTORS

BACKGROUND AND PRIOR ART

The present invention relates to recombinant DNA technology and more specifically to the structure and function of DNA vectors for the transfer, replication and expression of heterologous DNA inserted within the DNA vector.

The structure and operating principles of DNA vectors, which are of primary importance in recombinant DNA technology, have been set forth in the prior art, for example, in Cohen et al., U.S. Pat. No. 4,237,224. A DNA vector is a self-replicating entity, usually of plasmid or phage origin, having certain unique restriction sites permitting the insertion of heterologous DNA at a locus which is non-essential for vector replication. Preferably, insertion results in the alteration of some non-essential but detectable function as a result of splitting the gene coding for that function on the vector. Insertion of heterologous DNA at the desired site results in loss of the detectable function, thereby enabling the investigator to distinguish vectors having inserts from those lacking inserts by the characteristics conferred upon cells containing such vectors. Drug resistance genes have been widely used for such selection purposes. Unmodified vectors may confer upon host cells that carry them resistance to an antibiotic, such as ampicillin. Insertion of heterologous DNA within the ampicillin-resistance gene results in loss of the ampicillin resistance of host cells. Similarly, insertion of heterologous DNA within the region coding for the enzyme beta-galactosidase has permitted selection for bacterial colonies which lack beta-galactosidase activity. Screening for colonies having an active beta-galactosidase (Lac+ phenotype) is carried on agar plates containing the substrate analog 5-bromo-4-chloro-3-indolyl-beta-D-galactoside (hereinafter XG). Colonies expressing a Lac+ phenotype are stained blue as a result of enzyme activity hydrolyzing the substrate analog and releasing a blue dye while colonies which lack enzyme activity (Lac− phenotype) remain white. Transformation of a Lac− host strain by a vector carrying an intact and expressible lacZ gene (coding for beta-galactosidase) is manifested by blue colonies transformed to Lac+ phenotype. The presence of a heterologous insert in the vector disrupting the beta-galactosidase coding sequence on a vector (in a Lac− host) is detected by "white selection", the appearance of white colonies against a background of predominately blue colonies. (In this system, the background of untransformed Lac− host cells is eliminated by incorporating a drug resistance marker in the vector, and adding the drug to the growth medium on the plates so that only vector-transformed cells grow at all). Additional constraints on vector structure are required if the inserted heterologous DNA is to be expressed. Expression is a general term denoting the synthesis of a protein, a peptide or an RNA transcript by a cell. One manifestation is the synthesis of messenger RNA using the heterologous DNA as template. The fundamental requirements for expression in the form of protein or polypeptide coded by the inserted DNA are that the insert be adjacent to a promoter-translation start region, that the orientation of the insert be the same as the promoter-translation start region, that the insert be preceded by a translation start codon, and, if the insert lies within an existing coding region, that the existing and inserted coding regions be in the same reading frame phase.

Terms used herein are intended to have the meaning generally understood in the art. Thus, a promoter-translation start region is a segment of DNA which is normally untranslated but which functions in the initiation of transcription (messenger RNA synthesis) and in the initiation of translation of mRNA, for example, by providing a ribosomal binding site. A promoter-translation start region has a defined direction of action with respect to the vector as a whole, such that coding regions lying to one side are under its functional influence, whereas adjacent coding regions on the other side are unaffected by it. Coding regions affected by the promoter are said to be in a direction "downstream" of the promoter. The coding region itself is also directional, that part which codes for the amino terminal end of the protein for which it codes must lie nearest the promoter-translation start region, downstream therefrom, while the part coding for the —COOH terminal region of the protein must lie farthest from the promoter-translation start region. When the promoter-translation start region and coding region are properly disposed with respect to one another such that translation can occur as just described, they are said to be in proper orientation. Improper orientation occurs if the coding region is inserted backwards, such that the —COOH coding end is closer to the promoter-translation start region, or if the coding region is inserted upstream from the promoter. Reading frame refers to the manner in which adjacent nucleotides are clustered in groups of three, each group of three, or triplet, coding for an amino acid of a protein. The reading frame is established by the first ATG triplet (coding for methionine) which lies a few nucleotides, typically 11 to 17, downstream from the ribosomal binding site sequence of the promoter-translation start region. The reading frame must be maintained without interruption throughout the coding region. If an inserted DNA is to be expressed by joining it to an existing coding region, it must be joined in such a manner that the desired reading frame of the insert is the same as that of the coding sequence to which it is joined. The two reading frames are then said to be in phase. If the reading frames are out of phase, the integrity of the sequence of nucleotide triplets is interrupted in going from one coding region to the next, by the interposing of one or two extra nucleotides. Translation then continues, using nucleotide triplets established by the reading frame of the pre-existing coding region until a stop codon is encountered. It has been observed that stop codons are frequently encountered in coding sequences which are read incorrectly in either of the two alternative reading frames. In fact, the existence of an open reading frame, i.e., a reading frame in which no stop codon is encountered over a length sufficient to code for a polypeptide protein or fragment thereof, is considered presumptive evidence that the segment is in fact a coding segment in that reading frame.

The synthesis of proteins by genetically altered microorganisms is a major aspect of the multi-million dollar recombinant DNA industry. Virtually any useful protein, such as an enzyme, hormone or antigen, can be synthesized by such organisms, usually in amounts far exceeding conventional isolations. In any case, however, it is necessary first to clone a gene or DNA segment coding for the desired protein. The cloning is frequently the most difficult and problematic step.

A basic problem of cloning technology relates to the identification of clones containing a specific desired sequence against a background of clones containing other sequences. Most of the initial successes in cloning were obtained in systems where it could reasonably be expected that the desired cDNA was present in high proportion. Pre-purification of mRNA to select for mRNA in a desired size range was frequently employed. Where homologous sequences had previously been cloned, it was possible to identify the desired clones by hybridization, using the known sequence as a probe. The brute force technique of sequence analysis has also been employed, although chiefly in situations where only a few clones needed to be screened. At the present time, a need exists for techniques of general utility that would enable investigators to identify a clone containing the desired sequence under conditions where it may be necessary to screen a large number of clones in order to obtain a positive result, e.g., where the desired sequence is present in low proportion.

SUMMARY OF THE INVENTION

A class of vectors suitable for cloning and expression of coding DNA of inserted heterologous coding DNA is provided according to the invention, whereby many of the difficulties of selection and identification of specific coding sequences can be overcome. Vectors according to the invention uniquely provide for selection by restoration or acquisition of a measurable activity. An example embodying beta-galactosidase permits "blue" selection, where the insertion of a DNA segment results in the restoration of beta-galactosidase expression. The vectors thus provide for positive selection for insertion of heterologous DNA. Furthermore, the vectors are constructed in such a way that restoration of the positive selection function is dependent upon the existence of an open reading frame throughout the inserted heterologous DNA. As a consequence, any insert possessing an open reading frame in phase with a promoter and coding region on the vector results not only in positive selection for the existence of the insert but also for expression of that insert. It follows that it is now possible, using vectors of the present invention, to select in one step for insertion and expression of DNA coding in whole or in part for a protein. Antibodies may be raised against the protein or protein fragment thus expressed, thereby making it possible to assay for the protein independently of its function. Alternatively, where the cloning and expression of a predetermined protein is desired, it is possible to screen for expression of that protein among the blue colonies known to be expressing a protein or protein fragment of some sort. Thus, it is possible, using the vector of the invention, to clone and assay for any protein or expressible fragment without having any prior knowledge of the structure or function of the protein or of the structure of the gene coding for it.

The structural features of open reading frame vectors of the present invention which make these techniques possible include a promoter-translation start region functional in the host cell and adjacent thereto, and downstream therefrom, first coding segment having a start codon and codons for the —NH₂ terminal portion of a protein, an insertion region having an insertion site and a second coding segment coding for a detectable protein, where the insertion region is of such a length that the first and second coding segments are not in reading frame phase with each other. Translation initiated within the promoter-translation start segment yields correct translation of the first coding segment but incorrect translation of the second coding segment. Correct translation of the second coding segment, resulting in functional expression of the detectable protein coded thereby, occurs when a heterologous DNA segment of proper length is inserted in the insertion region so as to restore proper reading frame to the second coding segment. If the heterologous inserted DNA segment also has an open reading frame in phase with the correct reading frame of the second coding region, i.e., has no stop codons within that reading frame, it will be expressed along with the second coding segment. The resulting protein, expressed under control of the promoter-translation start segment, is a "tribrid" whose NH₂ terminal segment is contributed by the first coding segment, whose midsection is coded by the heterologous insert, and whose COOH terminal segment is coded by the second coding region. The second coding region is so chosen as to provide that the detectable protein coded by the second coding region will be functional as part of the expressed tribrid protein. The first and second coding regions will be out of phase with one another if the insertion region contains either one or two extra nucleotides over a multiple of three, beginning from the last full codon of the first coding segment. The reading frames of the first and second coding segments will be restored in phase by the insertion of a DNA segment of compensating length, having, at a minimum, two, or one nucleotide respectively, or in general, (3n+2) or (3n+1) nucleotides, where n is an integer. Both types of open reading frame vectors have been constructed, and are designated ORF-1 and ORF-2. ORF-1 requires insertion of (3n+2) nucleotides to restore the correct reading frame phase between the first and second coding segments, while ORF-2 requires an insertion of length (3n+1) nucleotides. It will be understood that the foregoing applies to insertions made by single restriction enzyme cuts which do not delete nucleotides from the vector. Either an ORF-1 or ORF-2 vector may be converted to another phase by deleting an appropriate number of nucleotides, for example, by double restriction cuts in the insertion region. Thus, it will be understood that an ORF-1 vector is convertable to an ORF-2 vector by deletion of (3n+2) nucleotides, and an ORF-2 vector is convertible to ORF-1 by deletion of (3n+1) nucleotides.

DETAILED DESCRIPTION OF THE INVENTION

Figure 1:
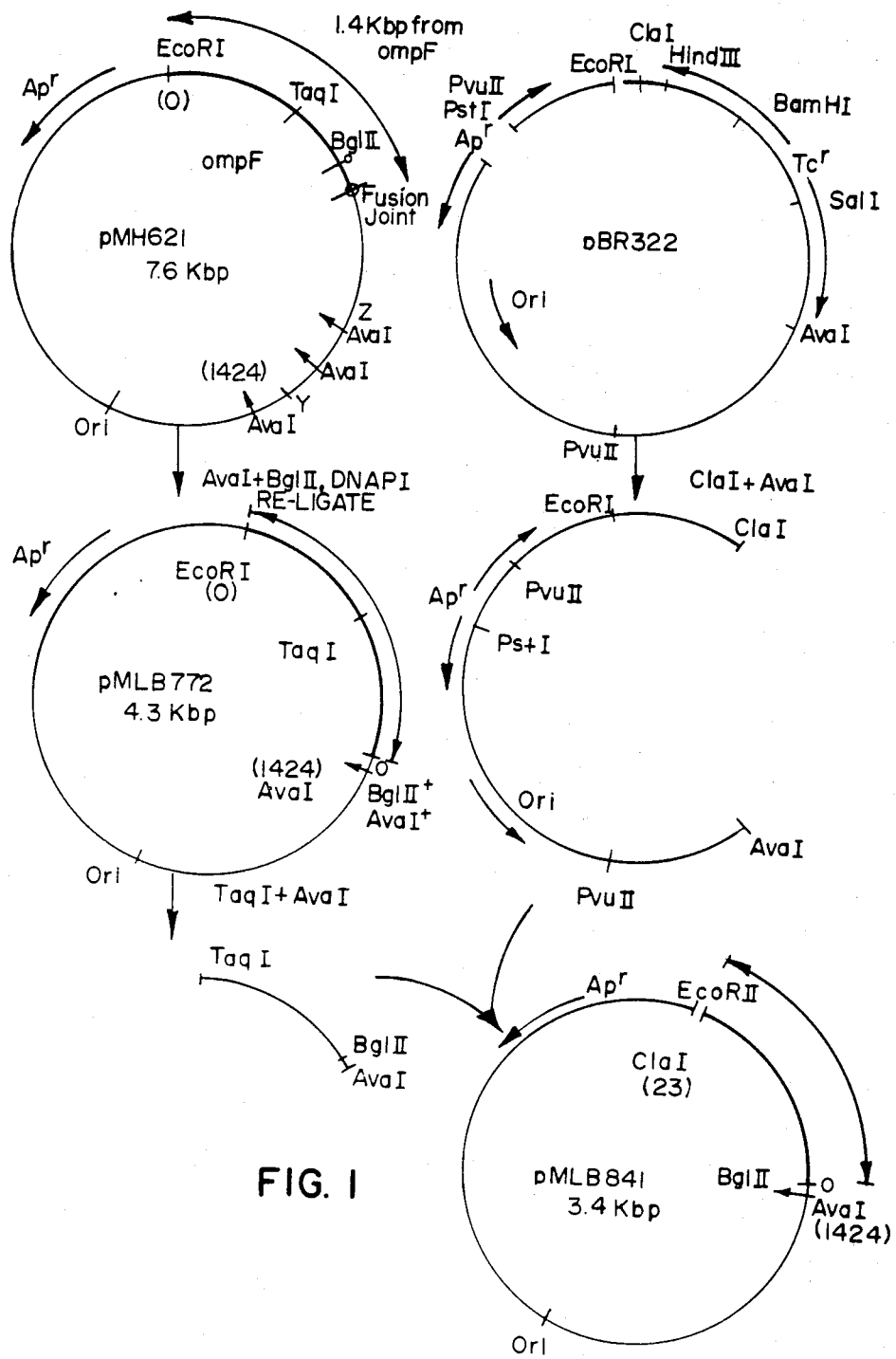
FIG. 1 shows a series of plasmid constructions leading to pMLB841.

The promoter-translation start region of an open reading frame vector may be any such region operative in the contemplated host cell. Where the contemplated host is *E. coli*, the promoter-translation start region should be one operative in *E. coli*, whereas if the contemplated host is, for example, yeast, a yeast promoter-translation start region must be provided. The promoter-translation start region may be chosen with additional characteristics in view including activity, controllability, and the like. The region need not be unique, but it must be borne in mind that inducible or derepressible promoters may require additional constraints, as will be understood in the art due to potential ancillary effects of full expression of the genes they regulate.

The first coding segment is most conveniently that normally associated with the promoter-translation start region. However, it may be derived from a different source, and it may code for part of the same, or a different protein from that of the second coding segment. There is no definite upper size limit for the first coding segment, although practical considerations operate to limit the size as much as possible, consistent with the goal of incorporating certain desired functions into the protein coded thereby. At a minimum, the first coding segment must include a start codon (ATG) appropriately spaced from the ribosomal binding site of the promoter-translation start region to function as the initiation point for translation. It may be advantageous to provide a first coding segment of sufficient length to code for a signal peptide to provide for transport of any protein or peptide connected thereto to the outer membrane or periplasm of the host cell. Preferably, the promoter-translation start region and first coding segment, for use in an E. coli host, are provided by the ompF gene of E. coli. The ompF promoter is very active, being responsible for one of the most abundant proteins of E. coli. Furthermore, the ompF promoter is under positive regulation by the product of ompB, a gene mapping remote from ompF. Temperature-sensitive or other conditionally active mutations in ompB can be incorporated into a host cell strain to enable the investigator to control the activity of the ompF promoter. In fact, an ompB− host, or growth conditions reducing the activity of the ompF promoter, are strongly preferred, to prevent cell death due to overproduction of the tribrid protein over several generations of growth. Sufficient residual ompF promoter activity is observed, even in ompB− strains, to permit expression of the Lac+ phenotype. As a further advantage, the ompF signal peptide is highly effective as a leader for transporting proteins to the cell exterior. For example, it is capable of transporting the large cytoplasmic enzyme beta-galactosidase to the outer cell membrane, a result which cannot be achieved with less active leader sequences. See Bedoulle, et al., *Nature*, 285, 78 (1980). See also Silhavy, et al., U.S. application Ser. No. 219,719, incorporated herein by reference. The ompF promoter-translation start region, together with a DNA segment coding for the signal peptide region of the OmpF protein, has been cloned and transferred to a plasmid vector, as described by Silhavy, et al, supra.

The structure of the insertion segment is dictated by the minimal constraints of length, either $(3n+1)$ or $(3n+2)$ nucleotides, as described supra, and by the requirement for a sequence incorporating an insertion site. An insertion site which is a restriction enzyme cleavage site and the only site on the vector sensitive to that enzyme, is greatly to be preferred. Even more preferably, the insertion segment sequence may incorporate a plurality of restriction sites not found elsewhere on the vector. The choice of which particular site or sites to employ is based upon considerations of convenience and is a matter of ordinary skill. The insertion segment contains no stop codon, specifically no TAA, TAG or TGA triplets, in any reading frame read in the direction of transcription. For convenience, an insertion site in the insertion segment, as just described, is termed herein a "designated" insertion site.

The second coding segment codes for a protein which is detectable when expressed, and the detection of which, enables one to distinguish cells or clones of cells which express the protein from those which do not. The means of detection may be any convenient means including, but not limited to, enzyme activity, specific antibody binding, drug resistance, and the ability to grow on specialized media. The second coding segment must be sufficiently complete that the protein which it expresses possesses the desired detectable activity, although the coding segment need not comprise the entire gene which normally codes for that protein. The detectable protein must be one which is capable of tolerating the addition of a polypeptide or protein at its —NH$_2$ end without substantial loss of function. This is so because the insertion at a designated insertion site of a heterologous DNA fragment containing an open reading frame and having the correct number of nucleotides to re-establish the first and second coding segments in the same reading frame will result in expression of a tribrid protein having the polypeptide moieties coded by the first coding segment and inserted heterologous DNA connected to the —NH$_2$ end of the protein coded by the second coding segment. Insertion of a heterologous DNA segment as described results in expression of the detectable function of the protein coded by the second coding segment.

The tribrid protein synthesized in the above-described manner has additional useful properties other than the detectable function resulting from expression of the second coding segment. For example, the tribrid protein has antigenic determinants associated with the protein or polypeptide coded by the heterologous inserted DNA. For convenience, this moiety is termed the mid-section of the tribrid protein. If the mid-section is all or a significant part of a known protein against which antibodies have previously been raised, the tribrid will bind such antibodies. The antibody binding may be detected by any of a large number of detection systems known in the art. It is therefore possible to screen positive colonies to detect those whose inserts code for a given antigen or antigenic protein fragment.

A more significant advantage is provided by the fact that antibodies can be made against any tribrid protein expressed as a result of an insertion in an open reading frame vector. Part of the antibody thus prepared will be directed against antigenic determinants of the midsection, coded by the heterologous inserted DNA. Therefore, knowing nothing about the structure or function of the protein or polypeptide comprising the midsection of the tribrid, it is possible to develop an immunoassay against the protein or polypeptide comprising the midsection. Those portions of the antibody preparation directed against determinants coded by the first or second coding segments may be cleared from the antibody preparation by adsorbing the preparation against purified preparations of the proteins or polypeptides comprising the first and second coding segments, respectively. Therefore, antibody directed solely and specifically against the protein or polypeptide of the midsection can be prepared. The use of open reading frame vectors for cloning is therefore useful to provide an assay for any protein, polypeptide, or fragment thereof, without regard to any prior information as to structure or function thereof. Subsequent analyses, screening procedures and tissue localization studies, using the antibody thus prepared, may be employed for the purpose of correlating additional information on the unknown protein or polypeptide. The vectors make it possible to construct an antibody library, with specific antibodies against every protein or polypeptide expressed by a given cell line. Furthermore, once a conventional antibody is available against a given antigen, it is possible, as a further refinement, to select for monoclonal antibodies also directed against that antigen. The antigens thus prepared, either conventional or monoclonal, may also be used in affinity chromatography to accomplish rapid and specific purification of the protein or polypeptide from its biological source material. All of this is made possible by the unique property of open reading frame vectors in providing positive selection for inserts providing an open reading frame and concomitant expression of such inserts as the midsection of a tribrid protein.

Successful use of open reading frame vectors is not dependent upon the insertion of DNA of any specific size. Of course it will be understood that the more useful information will be obtainable with larger inserts. Also, the likelihood of finding an open reading frame in a normally non-coding insert is reduced the longer the insert. False positive results remain a rare possibility, which may be excluded by recloning the insert in a vector of different reading frame, after removal or addition of nucleotides to alter the reading frame. The heterologous DNA is preferably cut by random nuclease action, thereby maximizing the probability that a fragment having the proper length to restore reading frame phase between the first and second coding segments of the vector will be generated in any given gene. The heterologous DNA may be either cDNA or genomic DNA. The use of cDNA provides a library of DNA fragments related, both in identity and frequency, to the proteins being expressed by the source tissue. The use of genomic DNA permits the cloning of fragments of all coding regions, whether expressed or not. The fact that eucaryotic genomic DNA coding segments are sometimes interrupted by introns does not substantially limit the usefulness of the vectors, since it is still possible to clone intact coding fragments of sufficient length to include specific antigenic determinants in the structure of the expressed protein or polypeptide fragment. A further advantage, when the ompF signal peptide is included in the first coding segment, is that the expressed tribrid protein is transported to the outer cell membrane. This obviates, or at least simplifies, purification of the tribrid protein prior to antibody formation, or other analytic procedures.

The construction of open reading frame vectors and their application for cloning and expressing a heterologous DNA insert are described in the following examples. In these examples, the techniques for cell growth, isolation of vector DNA, restriction enzyme cutting, DNA joining reactions, and DNA sequence analysis were those employed generally in the art. For example, see generally *Methods in Enzymology*, Vol. 68, 1979 (R. Wu, Ed.).

EXAMPLE 1

Construction of pORF-1.

The construction described herein was designed to provide a first coding segment and second coding segment out of reading frame phase with one another, being separated by a linker segment of DNA containing within its sequence one or more restriction sites unique to the vector which could therefore serve as insertion sites for heterologous DNA. For the first coding segment, the promoter-translation start region and coding segment for the signal peptide and first few amino acids of the OmpF protein was chosen because of the advantages conferred by its use, as described, supra. For the second coding segment, a majority of the *E. coli* lacZ gene coding for the enzyme beta-galactosidase was chosen, since its functional attributes meet the requirements set forth, supra, and the expression of the enzyme can be detected by "blue" selection, as described, supra, using a lac− host cell strain.

The promoter-translation start region and first coding segment of ompF had been previously cloned on a plasmid vector, designated pMH 621, described in U.S. patent application Ser. No. 219,179, incorporated herein by reference as though set forth in full. Nucleotide sequence analysis of this vector revealed that the ompF region, containing the promoter, translational start region and coding region for the —$NH_2$ terminal amino acids of the signal peptide and first 12 amino acids of mature OmpF were contained within a 452 base pair fragment flanked by a TaqI site upstream from the promoter and a BglII site downstream from the promoter. While it would have been feasible to insert the TaqI-BglII ompF fragment directly into a suitable site, such as the BamHI site of pBR322, such an expedient would have resulted in loss of both sites in the recombinant, making further insertions downstream from the ompF region difficult. A series of subcloning steps was therefore devised, to preserve the useful BglII site downstream from ompF and to make other subcloning steps possible as well. The devising of such steps is part of the ingenuity and invention of vector construction. In order to transfer the ompF fragment and retain its intact BglII site, the OmpF gene fragment was subcloned as follows: plasmid pMH 621 was cleaved by a combination of restriction enzymes AvaI and BglII, then treated with *E. coli* DNA polymerase I to fill in the single-stranded ends generated by the restriction enzyme cleavage. The plasmid was then re-ligated. Restriction enzyme cleavage as described resulted in deletion of approximately 3.5 kb lying between the AvaI and BglII sites, and generated overlapping BglII and AvaI sites at the ompF plasmid joint downstream from the ompF promoter. This intermediate plasmid was designated pMLB772. Cleavage of pMLB772 with a combination of TaqI and AvaI restriction enzymes yielded a 456 base pair fragment containing the desired ompF region. This fragment was then inserted into plasmid pBR322 previously cleaved with a combination of ClaI and AvaI. The resulting plasmid, designated pMLB 841, has the desired ompF region in place of the tet gene of pBR322. DNA sequence analysis of pMLB841 demonstrated that the desired ompF region was left intact and unaltered by the foregoing sequence of manipulations, and that the BglII site remained intact. The series of plasmid constructions just described is diagrammed in FIG. 1. The plasmid pMLB841 was used as the source of the ompF region in constructing the open reading frame vector.

Figure 2:
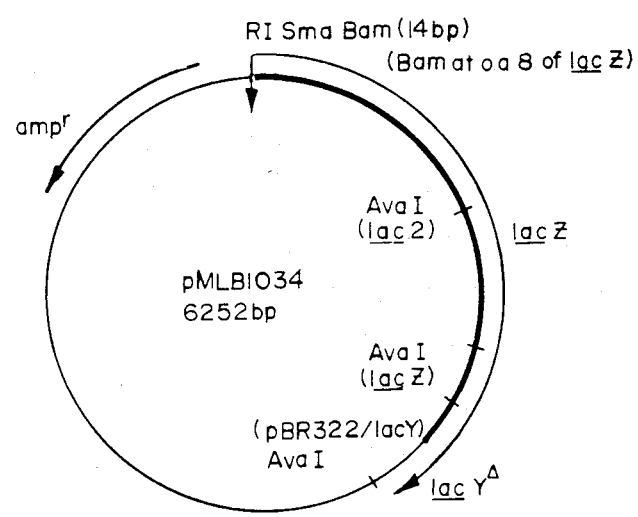
FIG. 2 shows plasmid pMLB1034.

DNA coding for the second coding segment comprising all of the region essential for coding for functional beta-galactosidase was derived from plasmid pMLB1034. The plasmid pMLB1034 is a 6.2 kb derivative of pMC871, described by Casadaban, M.J., et al., *J. Bact.*, 143, 971 (1980). Combined digestion of pMC871 with BamHI and SalI endonucleases yielded a 7.1 kb fragment comprising the lacZ and lacY genes. The fragment was cloned within the BamHI and SalI sites of plasmid pBR322 (Bolivar, F., et al., Gene, 2, 95 (1977)). The modified plasmid, designated pMBL403, was selected as yielding ampicillin resistant, Lac+ transformants. Partial AvaI digestion of pMLB403 followed by religation deleted a 3660 bp fragment comprising most of the lacY gene and additional DNA distal thereto, and to the lacZ gene. After religation, the resulting plasmid, designated pMLB508, was approximately 7600 bp in length and conferred Lac+ phenotype to transformants. The lac region included the entire lacZ gene and the start of the lacY gene through amino acid 70. Further manipulations, including removal of an RI-HindIII fragment yielded a plasmid having the desired lacZ region coding for amino acid 8 immediately preceded by a linker containing the following restriction sites: EcoRI - SmaI - BamHI. This plasmid is designated pMLB1034, diagrammed in FIG. 2. The lacZ DNA is not expressed, since there is no translation start site or ribosomal binding site, and the DNA encoding the first 7 amino acids of lacZ are missing. However, insertion of DNA sequences encoding amino acids in frame with lacZ and providing a protein translation start site (a ribosome binding site and the codon ATG) will result in expression of active beta-galactosidase. In proof thereof, a fusion at the BglII site at amino acid 12 of ompF to the BamHI site at amino acid 8 of lacZ and pMLB 1034 produced an active hybrid beta-galactosidase.

Figure 3:
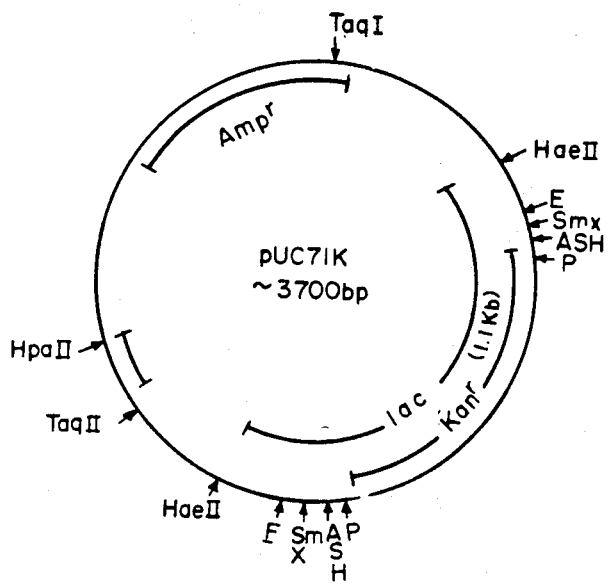
FIG. 3 shows a diagram of pUC71K together with the polylinker sequence flanking the Kan$^R$ fragment.

An intermediate sequence, to disrupt reading frame and provide multiple potential designated insertion sites between the first and second coding segments, was derived from a "poly-linker" segment surrounding a kanamycin resistance determinant (Kan$^R$) on the plasmid pUC71K (The Kan$^R$ determinant is derived from Tn601 and is inserted into a plasmid, pUR-2, described by Ruther, U., Molec. Gen. Genet., 178, 475 (1980).The polylinker sequence was originally obtained by chemical synthesis. FIG. 3 shows a diagram of pUC71K together with the polylinker sequence flanking the Kan$^R$ fragment.) The structure of the poly-linker segment is: EcoRI - SmaI - BamHI - SalI - PstI - Kan$^R$ - PstI - SalI - BamHI - SmaI - EcoRI. In the construction described herein, the BamHI - Kan$^R$ fragment was employed.

The promoter-translation start and first coding segment, the intermediate segment and the second coding segment were united in a single plasmid by combining (1) a 478 bp EcoRI - BglII ompF region from pMLB 841, (2) the BamHI - Kan$^R$ fragment, and (3) the lacZ fragment of pMLB 1034 cut with EcoRI and BamHI endonucleases. These DNAs were mixed and joined with T4 DNA ligase. The resulting product was used to transform E. coli to kanamycin resistance. The resulting plasmid, designated pMLB 1039, has the BamHI - Kan$^R$ fragment lying between the BglII site in ompF and the BamHI site in lacZ.

Plasmid pMLB 1039 was then digested with endonuclease SalI and religated, thereby deleting the kanamycin resistance determinant but restoring the reading frame between ompF and lacZ. Transformants with the resulting plasmid designated pMBL 1053 were lacZ+, giving blue colonies, where the host cell strain was lac−.

The final step in the construction of pORF-1 was the insertion of the following synthetic DNA into the adaptor into the unique BamHI site: 5′-p GATCCCCG GG-OH 3′. This adaptor duplicates the BamHI site and introduces 5 additional base pairs (as a SmaI site) thereby interrupting the reading frame and preventing translation of the ompF - lacZ hybrid. The resulting plasmid, pORF-1, is therefore lacZ−. The restriction sites resulting from the foregoing construction, located in the intermediate region between ompF and lacZ are:

(ompF) - SalI - BamHI - SmaI - BamHI - (lacZ).

Figure 4:
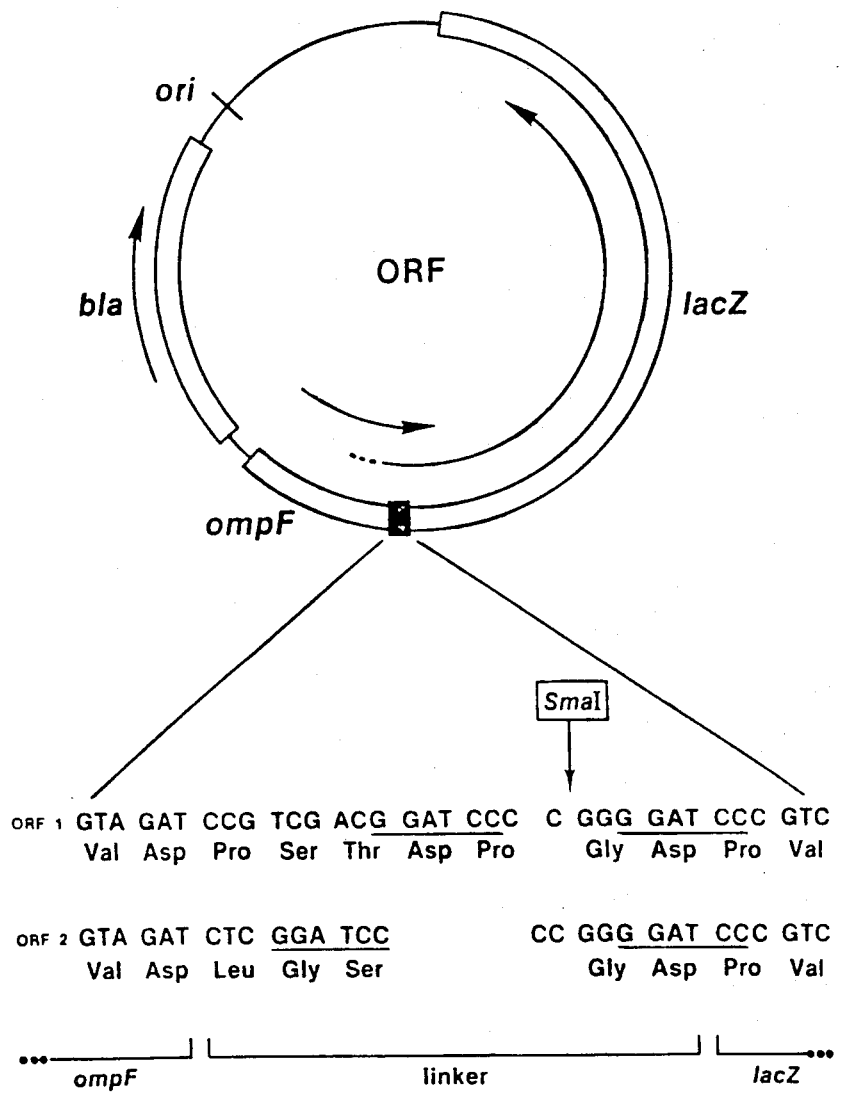
FIG. 4 shows the general construction of the open reading frame vector pORF-1.

FIG. 4 shows the general construction of the open reading frame vector pORF-1, giving the relevant sequence in the intermediate region between the first and second coding segments, as determined by DNA sequence analysis.

EXAMPLE 2

Vector pORF-2 was constructed in a slightly different manner from that described in Example 1, using sequential insertions. First, an AvaI fragment containing the Kan$^R$ determinant from pUC71K was inserted into pMLB 1034 at the SmaI site, cleaved with XmaI endonuclease, which recognizes SmaI sites but cuts them to leave sticky ends. The SmaI site is also sensitive to AvaI, which generates ends complementary to those generated by XmaI. Therefore, insertion restored the SmaI site on both sides of the Kan$^R$ determinant, giving the following arrangement:

EcoRI - SmaI - BamHI - SalI - PstI - Kan$^R$ - PstI - SalI - BamHI - SmaI - BamHI - (lacZ).

Digestion of the resulting plasmid with a combination of SalI and EcoRI endonucleases removed the region spanning the EcoRI site to the SalI site containing the Kan$^R$ determinant. To this cut plasmid was added the 482 base pair EcoRI - AvaI fragment from pMBL 841 containing the ompF region. At the junction between the AvaI site of the ompF fragment and the SalI site of the plasmid, the unpaired ends were complementary except for a single base pair mismatch, marked by "X" as shown:

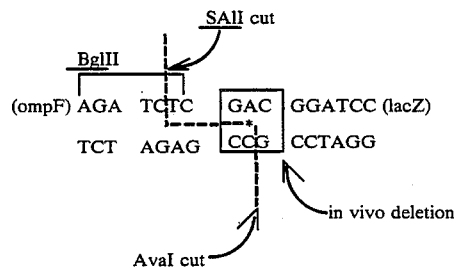

Transformation with the resulting plasmid resulted in a 3 base pair deletion at the mismatch site, as a fortuitous result of host cell repair. The extent of the repair deletion was not predictable in advance, but was determined subsequently by DNA sequence analysis. Other clones could yield vectors having deletions larger or smaller than that found. Hence, the method employed for the construction of this vector could in principle be used as a general method for the construction of vectors having either (3n+1) or (3n+2) intermediate insertions between the first and second coding segments. The resulting vector, designated pORF-2, has the following sequence of unique restriction sites at the ompF lacZ fusion joint: (ompF) BglII - BamHI - SmaI - BamHI - (lacZ). The structure of the vector in the region of the fusion joint was confirmed by DNA sequence analysis, the results of which are shown in FIG. 4.

EXAMPLE 3

The functional properties of an open reading frame vector are demonstrated by the insertion and expression of the thymidine kinase (tk) gene of Herpes virus.

The DNA sequence of the Herpes virus tk gene is known from the work of Wagner, M.J., et al., *Proc. Nat. Acad. Sci. USA* 78, 1441 (1981). Inspection of the sequence revealed that a 305 bp fragment generated by BglII and AvaI restriction endonuclease cleavage could be inserted into pORF-2 between the BqlII and XmaI (SmaI) sites. The 305 bp fragment would re-establish an open reading frame in phase with the ompF and lacZ reading frames, realigned by the double restriction cut. The BglII site in the tk fragment is located 57 bp before the start of translation of tk. Although not translated in the intact tk gene, this 57 bp sequence nevertheless has an open reading frame in phase with a translated region, and will be translated as part of the tribrid protein expressed in the pORF-2 vector. The AvaI site is located 248 bp beyond the start of tk translation and cleavage is in the codons for amino acids 82 and 83 of the tk protein. Thus, when the BglII-AvaI fragment is expressed in pORF-2, a 102 amino acid sequence is made, of which the first 17 amino acids are not expressed in the intact tk gene, and the last 83 amino acids are identical with the amino terminus of thymidine kinase protein. The source of tk DNA for construction of the pORF-2-tk hybrid was pMH621-tk, a derivative of pMH621 where a BglII-BamHI fragment of the Herpes virus chromosome, containing the tk gene, has been inserted at the BglII site of pMH621.

The tk gene, inserted at the BglII site of pMH 621, was removed therefrom by digestion with BglII and AvaI restriction enzymes. The plasmid pORF-2, described in Example 2, was digested with BglII and XmaI (which cuts at the SmaI site generating 4 bp sticky ends) to provide an insertion locus for the tk gene fragment. The digests were mixed, ligated and transformed into ompB−, lacZ− cells. A number of LacZ+ colonies were obtained, and from these, a plasmid yielding predicted size distribution on restriction enzyme miniscreens was chosen for further study. This plasmid was designated pORF2-tk. The pORF-2 hybrid was transformed into *E. coli* MH-2000, ATCC accession No. 31,775, bearing a spontaneous ompB cold sensitive mutation (ompRcs-1) which gave maximal expression of ompF promoter at 42° C. and greatly reduced expression at 30° C. The transformed strain was grown at 30° C., then shifted to 42° C. Extracts from both temperatures were analyzed on SDS polyacrylamide gels. A high molecular weight protein, corresponding to the ompF-tk-lacZ tribrid protein, was observed in both 30° and 42° cultures; however, higher amounts were present in the 42° cultures. The 42° extracts were then run on preparative gels, the tribrid protein band was removed and electroeluted. The 83 amino and thymidine kinase fragment was calculated to constitute about 2% of the total tribrid molecular weight.

Approximately 100 μg of the electroeluted protein was mixed with Freund's adjuvant and injected into a goat, using a conventional immunization technique. In the fourth week following the single injection, a sample of the goat's blood serum was obtained for antibody analysis. The presence of anti-tk antibody was tested using extracts of cultured cells infected with Herpes virus and grown in the presence of [$^{35}$S] to label proteins. Control cells, either uninfected, or infected with a Herpes virus mutant lacking thymidine kinase, were similarly labeled. Cell extracts were reacted with the goat serum under standard conditions for immunoprecipitation. The precipitates were analyzed by sodium dodegel sulfate gel electrophoresis, and the [$^{35}$S] protein bands visualized by autoradiography. A single clear band that comigrated with authentic thymidine kinase was observed in extracts of infected cells that was not present in either uninfected or tk-infected controls. Therefore the tribrid protein, having a fragment of thymidine kinase incorporated in its midsection, elicited specific antibody against thymidine kinase.

The open reading frame vectors described in the foregoing examples, pORF-1 and pORF-2, have been deposited at the American Type Culture Collection, 12301 Parklawn Drive, Rockville, Md. 20852, in connection with the instant case. Plasmid pORF-1, ATCC accession No. 39,148, was deposited on 6-16-82, 1982. Plasmid pORF-2, ATCC accession No. 39,146, was deposited on 6-16-82, 1982.

What is claimed is:

1. An open reading frame DNA vector having a promoter-translation start region, and adjacent thereto and downstream therefrom, a first coding segment having a start codon, a second coding segment coding for a detectable protein, and an insertion region between said first and second coding regions having no stop codons in frame with either the first or the second coding segment, and said insertion region having an insertion site and being of such length that the first and second coding segments are not in reading frame phase with each other.

2. An open reading frame vector according to claim 1 wherein the promoter-translation start region is that of the ompF gene of *E. coli*.

3. An open reading frame vector according to claim 1 wherein the second coding segment codes for a functional fragment of beta-galactosidase.

4. An open reading frame vector according to any of claims 1, 2 or 3 wherein the number of insertion sites in the insertion region is greater than one.

5. An open reading frame vector according to claim 1 wherein the insertion of a segment of heterologous DNA possessing an open reading frame in phase with said first coding region, said heterologous DNA being $(3n+1)$ nucleotides in length, where n is an integer, restores the reading frame between said first and second coding segments without the creation of stop codons in that reading frame whereby said first and second coding segments and said heterologous DNA are in reading frame phase with one another.

6. An open reading frame vector according to claim 1 wherein the insertion of a segment of heterologous DNA possing an open reading frame in phase with said first coding region, said heterologous DNA being $(3n+2)$ nucleotides in length, where n is an integer, restores the reading frame between said first and second coding segments without the creation of stop codons in that reading frame whereby said first and second coding segments and said heterologous DNA are in reading frame phase with one another.

7. An open reading frame vector according to claim 5 wherein the promoter-translation start region and first coding segment are derived from the *E. coli* ompF gene and the second coding segment codes for an active fragment of the *E. coli* beta-galactosidase gene.

8. An open reading frame vector according to claim 6 wherein the promoter-translation start region and first coding segment are derived from the *E. coli* ompF gene and the second coding segment codes for an active fragment of the *E. coli* beta-galactosidase gene.

9. A method for cloning and positive selection from a cDNA or genomic DNA preparation, of a DNA segment having an open reading frame comprising the steps of:
   (a) inserting the cDNA or genomic DNA in the insertion region of an open reading frame vector having a promoter-translation start region, and, adjacent thereto and downstream therefrom, a first coding segment having a start codon, a second coding segment coding for detectable protein, and an insertion region joining the first and second coding segments having no stop codons in frame with either the first or the second coding segment, and said insertion region having an insertion site and being of such length thet the first and second coding segments are not in reading frame phase with each other, the cDNA or genomic DNA preparation comprising a DNA segment or length sufficient to restore the reading frame phase between said first and second coding regions, without the creation of stop codons in that reading frame, whereby insertion of said segment permits expression of said second coding region by synthesis of said detectable protein,
   (b) transforming a host cell strain with the open reading frame vector having inserted DNA, and
   (c) selecting the transformants expressing the second coding region by detecting the protein coded thereby, said transformants containing an inserted cDNA or genomic DNA segment having an open reading frame.

10. The method of claim 9 wherein the open reading frame vector is of the ORF-1 type and the inserted cDNA or genomic DNA segment is of length $(3n+2)$ nucleotides, where n is an integer.

11. The method of claim 9 wherein the open reading frame vector is of the ORF-2 type and the inserted cDNA or genomic DNA segment is of length $(3n+1)$ nucleotides, where n is an integer.

12. The method of claim 9 wherein the promoter-translation start region and first coding segment of the open reading frame vector are derived from the *E. coli* ompF gene and the host cell transformed in step (b) has ompB$^-$ genotype.

13. The method of claim 9 wherein the second coding region of the open reading frame vector codes for a functional fragment of *E. coli* beta-galactosidase and the host cell transformed in step (b) is pheotypically Lac$^-$, whereby transformants are selected in step (c) by detecting beta-galactosidase activity in colonies thereof.

14. A method of identifying and quantifying a protein or polypeptide, without regard to its structure or biological function, comprising the steps of:
   (a) expressing a DNA segment of $(3n+1)$ or $(3n+2)$ nucleotides length, where n is an integer, coding for the protein, polypeptide or a fragment thereof, as the midsection of a tribrid protein produced by a microorganism, the microorganism being transformed by an open reading frame vector in which the DNA segment has been cloned, wherein the open reading frame comprises a promoter-translation start region, and adjacent thereto and downstream therefrom, a first coding segment having a start codon, a second coding segment coding for a detectable protein, and an insertion region between said first and second coding regions having no stop codons in frame with either the first or the second coding segment, and said insertion region having an insertion site and being of such length that the first and second coding segments are not in reading frame phase with each other,
   (b) separating the tribrid protein from other proteins produced by the microorganism,
   (c) making an antibody preparation against the tribrid protein by immunizing an animal against the tribrid protein, the antibody preparation comprising antibody specifically reactive with the mid-section of the tribrid protein,
   (d) reacting the antibody preparation with a protein solution comprising the protein or polypeptide to be identified or quantified, whereby reaction of that antibody specifically reactive to the midsection of the tribrid protein with a protein of the solution serves to identify and to quantify that protein, without regard to its structure or biological function.

15. A method of identifying a DNA segment coding for a protein, polypeptide or fragment thereof, against which an anitbody reactive to said protein, polypeptide or fragment thereof has been prepared, comprising the steps of:
   (a) inserting DNA segments of length $(3n+1)$ or $(3n+2)$ nucleotides, where n is an integer, said segments comprising the DNA segment to be identified, in an open reading frame vector, at the designated insertion site thereof, wherein the open reading frame vector comprises a promoter-translation start region, and adjacent thereto and downstream therefrom, a first coding segment having a start codon, a second coding segment coding for a detectable protein, and an insertion region between said first and second coding regions having no stop codons in frame with either the first or the second coding segment and said insertion region having an insertion site and being of such length that the first and second coding segments are not in reading frame phase with each other, whereby any such inserted DNA segment having an open reading frame is expressed as a tribrid protein whose midsection is coded by the inserted segment and whose —COOH terminal segment is a protein having a detectable function,
   (b) transforming a host microorganism with the vector having an inserted DNA segment,
   (c) selecting colonies of transformed cells expressing the function of the protein comprising the —COOH region of the tribrid protein, and
   (d) screening the selected colonies with the antibody to detect expression of the protein, polypeptide or fragment thereof as the mid-section of a tribrid protein, coded by the DNA segment inserted in the vector.

* * * * *